(12) United States Patent
Temple

(10) Patent No.: US 7,857,138 B2
(45) Date of Patent: Dec. 28, 2010

(54) APPARATUS AND METHOD FOR DELIVERY OF MEDICATION

(76) Inventor: Mary Darlene Temple, 8325 Hilltop Circle Dr., Imperial, PA (US) 15126

( * ) Notice: Subject to any disclaimer, the term of this patent is extended or adjusted under 35 U.S.C. 154(b) by 1331 days.

(21) Appl. No.: 10/725,806

(22) Filed: Dec. 2, 2003

(65) Prior Publication Data

US 2005/0119622 A1    Jun. 2, 2005

(51) Int. Cl.
*B65D 71/00* (2006.01)
(52) U.S. Cl. ..................................... 206/571
(58) Field of Classification Search .............. 206/571, 206/572, 363, 364, 365, 370, 438, 570
See application file for complete search history.

(56) References Cited

U.S. PATENT DOCUMENTS

| | | | |
|---|---|---|---|
| 720,381 | A | 2/1903 | Ranger |
| 2,591,046 | A | 4/1952 | Brown |
| 4,195,734 | A | 4/1980 | Boner et al. |
| 4,469,482 | A | 9/1984 | Lissenburg et al. |
| 4,657,138 | A | 4/1987 | Watson |
| 1,650,980 | A | 11/1987 | Campbell |
| 5,062,828 | A | 11/1991 | Waltz |
| 5,289,919 | A * | 3/1994 | Fischer ...................... 206/571 |
| 5,850,917 | A | 12/1998 | Denton et al. |
| 5,941,394 | A * | 8/1999 | Siegler ....................... 206/571 |
| D416,196 | S | 11/1999 | Noble |
| D424,801 | S | 5/2000 | Spinelli |
| 6,132,416 | A | 10/2000 | Broselow |
| 6,454,097 | B1 * | 9/2002 | Blanco ....................... 206/570 |
| 6,460,702 | B2 * | 10/2002 | Hammond .................. 206/570 |

OTHER PUBLICATIONS

American Diabetes Association, "Eye Care and Retinopathy", http://www.diabetes.org/info/complications/retinopathy/default.jsp.
National Diabetes Information Clearinghouse, "National Diabetes Statistics", http://www.niddk.nih.gov/health/diabetes/pubs/dmstats/dmstats.htm.
M. Malone, "Comparison Between Methods for Determination of Glycosylated Hemoglobin A1C Levels in Subjects with Normal and Atypical Hemoglobins", Dept. of Pathology, Univ. of Pittsburgh School of Medicine. Pgh. PA 15213. http://path.upmc.edu/showcase/posters/alc.htm.
A. Aries, Ph.D., Effective Color Contrast, Arlene R. Gordon Research Institute, Lighthouse International, 111 E. 59th St., NY,NY 10022-1202, http://www.lighthouse.org/color_contrast.htm.
D.W. Guthrie, R.N., "The Diabetes Sourcebook", 5th Edition, McGraw-Hill, pp. 15-29, 58-59, 100-115.
Diabetes Forum, "Diabetes Mellitus and Insulin Storage", http://www.diabetesforum.net/eng_treatment_DM_Insulin_storage.htm.
B.A. Carlisle et al., "101 Medication Tips for People with Diabetes", Chapters 4-6, pp. 41-65, American Diabetes Association.

* cited by examiner

*Primary Examiner*—Jacob K Ackun, Jr.

(57) ABSTRACT

An apparatus and method for delivery of medication is provided. The invention includes a system for organizing and storing pre-determined dosages of medication by matching indicia on both the storage apparatus and the apparatus containing the medication. The invention allows visually-impaired, elderly, or those unable to read conventional indicia to determine the appropriate dosage of medication and to safely select and take the medication in the appropriate pre-determined dosage indicated by the indicia on the storage apparatus matching the indicia on the apparatus containing the medication.

5 Claims, 15 Drawing Sheets
(14 of 15 Drawing Sheet(s) Filed in Color)

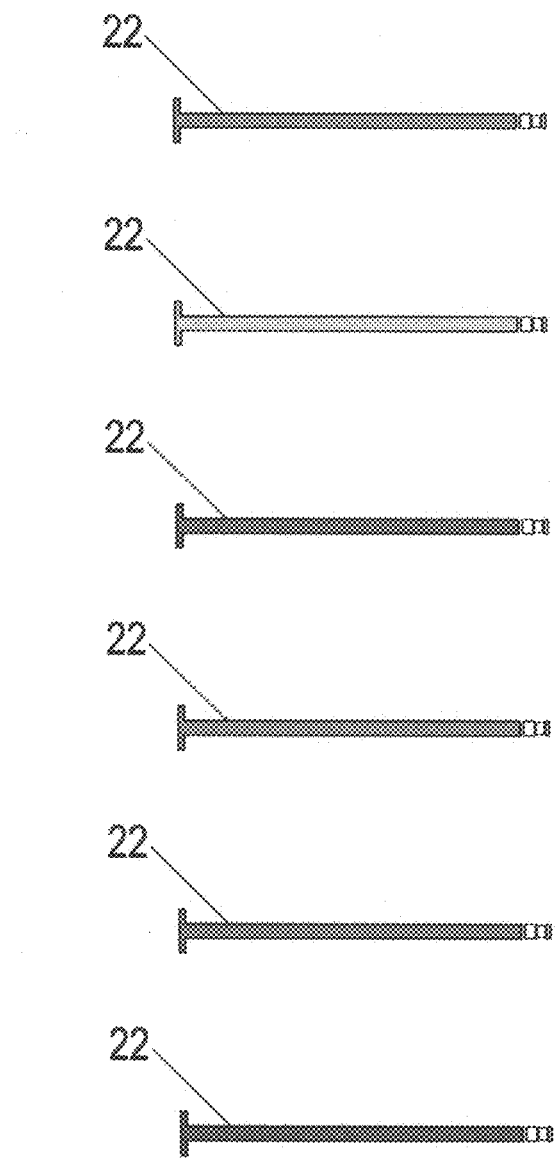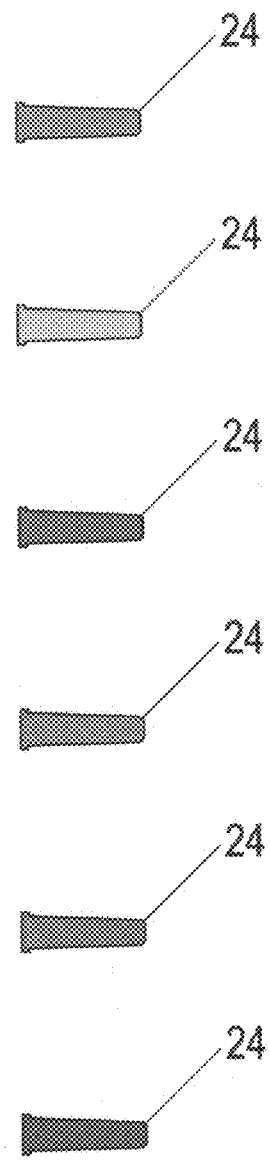

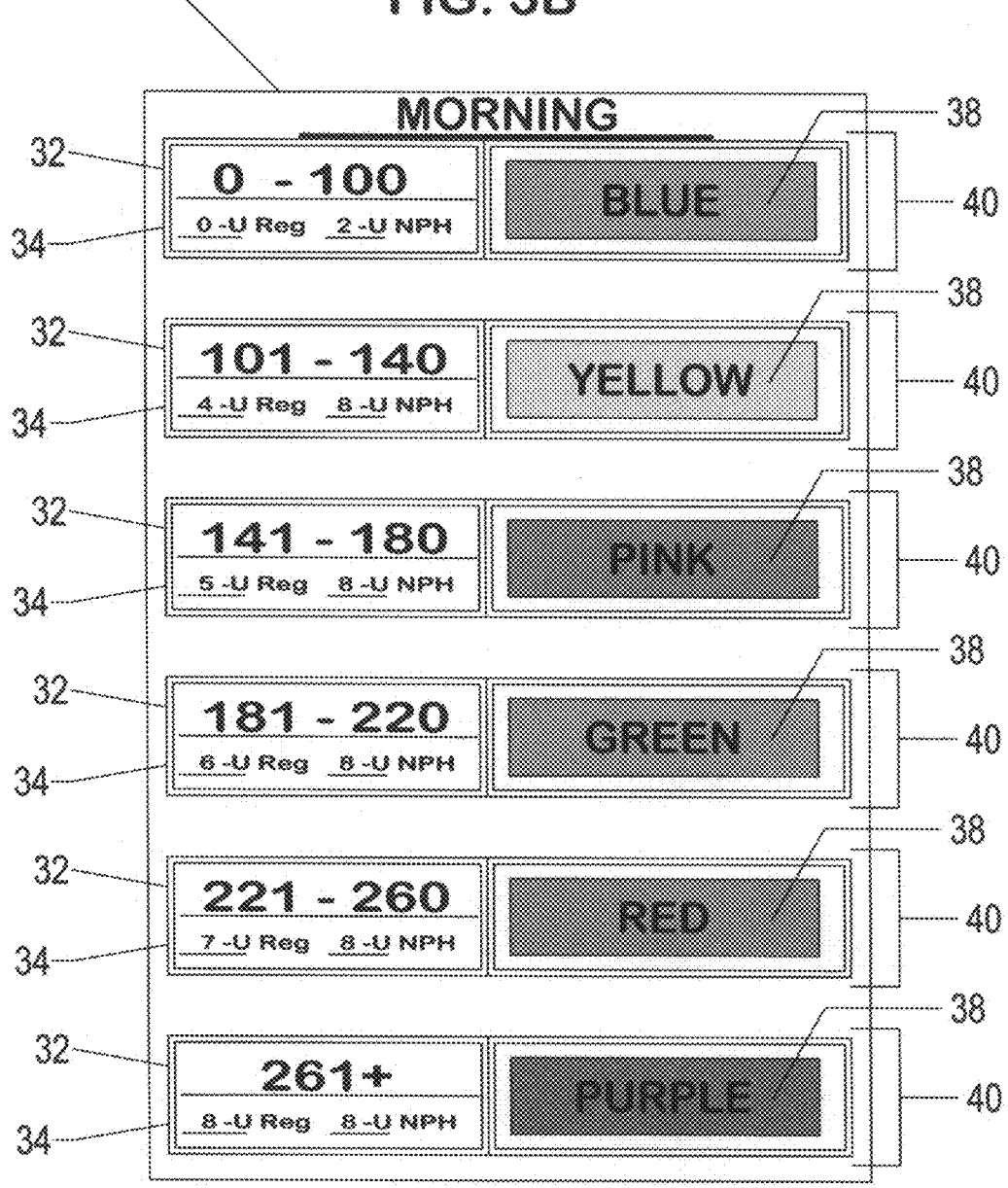

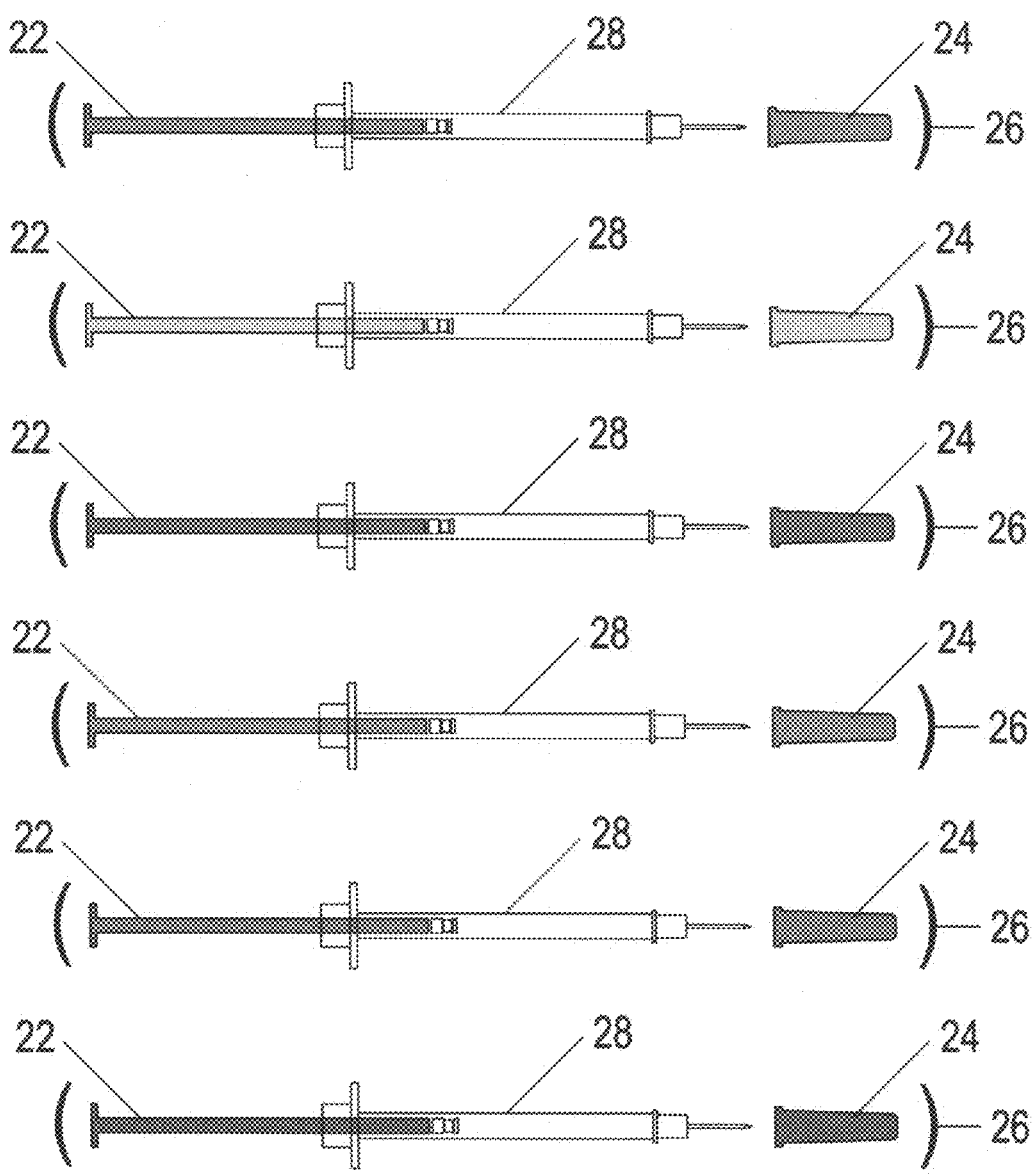

APPARATUS AND METHOD FOR DELIVERY OF MEDICATION

FIELD OF THE INVENTION

The present invention relates to a medication delivery method and apparatus, and in particular to a method and apparatus for organizing and delivering pre-determined dosages of medication.

BACKGROUND OF THE INVENTION

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization.

Diabetes is one of the leading public health problems in America today. As reported by the American Diabetic Association approximately 17 million people in the United States, or 6.2% of the population, has diabetes. Diabetes was the sixth leading cause of death listed on U.S. death certificates in 1999 accounting for 19 percent of all deaths that year. Of the 17 million of Americans who have diabetes, approximately 7 million, or 20.1 percent are 65 years of age and older. A staggering one million people are diagnosed with diabetes each year.

Many medical complications are the direct result of diabetes. Ocular complications such as diabetic retinopathy are the leading cause of new cases of legal blindness in people ages 20 to 74 in the United States. The risk for lower extremity amputation is 15 times greater in individuals with diabetes than in individuals without it. Kidney disease is a frequent and serious complication of diabetes. Approximately 30 percent of all new patients in the United States being treated for end-stage renal disease have diabetes.

The economic burden of diabetes is enormous. Each year patients with diabetes or complications from diabetes spend 50 million in-patient days in hospitals. A conservative estimate of total annual costs attributed to diabetes is at least $50 billion (American Diabetes Association estimate, 2002); however, the full economic impact of this disease is even greater because additional medical expenses often are attributed to the specific complications of the disease rather than to diabetes itself.

The risk of complications occurring in diabetics can be greatly reduced if the patient maintains good control of his/her blood glucose levels. Good control of blood glucose levels can be defined as having an adequate amount of insulin to utilize the amount of glucose in the body. Quantitatively, this blood glucose control is measured by determining the glycosylated hemoglobin level in patients over a two to three month period and is referred to as the determination of the patient's Hemoglobin A1c (HbA1c). The presence of glucose in the circulation results in a concentration dependent nonreversible covalent glycosylation of hemoglobin, forming hemoglobin sub-fractions A1a, A1b and A1c. Given the 120 day life span of the average human red blood cell, it is therefore possible to assess overall glucose levels in patients over the past two to three months by measuring the concentration of this glycosylated hemoglobin fraction A1c. The A1c fraction is based on the mathematical formula: % A1c=% GHb+1.76/1.49.

Reduction of glycemic or blood glucose concentrations in patients with diabetes mellitus prevents the development of diabetic complications. Currently, good blood glucose control is difficult to achieve in many patients with diabetes due to their inability to visually or cognitively perform the functions necessary to achieve optimum results. Examples of patients who are most at risk for complications because of poor blood glucose control are, but not limited to, the elderly, the very young, the visually or cognitively impaired and handicapped diabetics.

The obstacles that these patients encounter are endless. Among these obstacles are the proper administration of insulin dosages. Insulin is commonly delivered via syringes in specified doses during different intervals of time throughout the day. The current standard insulin syringe is clear, small, and utilizes incremental dosage markings that are very small and difficult to read. Diabetics with retinopathy and other ocular disorders have extreme difficulty seeing the small markings on the insulin syringe. Current remedies involve the enhancement of said markings, see for example, U.S. Pat. No. 720,381 (1903), for Hypodermic Syringe.

In patients with moderate to severe visual impairment the magnification or enhancement processes currently in use are often not an adequate solution to ensuring correct dosing. The ability to dispense medication at the proper time is another obstacle. Methods to store timed medication have been developed. Representative examples are seen in U.S. Pat. No. 1,650,980 (1927), for Case, U.S. Pat. No. 5,850,917 (1998), for syringe dosage tracking device with cooling feature, and U.S. Pat. No. 4,195,734 (1981), for apparatus for transporting medication and the like. Although these devices provide a suitable means for the storing and transporting of insulin, they are not designed to provide a safe and systematic approach for total diabetic management, especially for inpatients with limitations.

Often persons with insulin-dependent diabetes mellitus require several injections per day. In patients who have difficulty understanding directions or have visual impairment, caregiver intervention is required to ensure safe dosing. This requires that the caregiver be present to prepare each daily injection, which places extreme limitations on the caregiver as well as the patient. It often becomes necessary for the patient to live with a caregiver to accommodate the medication schedule, placing great burden on both the caregiver and patient. If professional health care is the only alternative available to the patient, the costs of frequent home visits to prepare medication is an enormous burden. It not only drains the lifetime limit on personal medical insurance, it becomes a major component of the problem of rising health care costs.

Patients with diabetes should not have to live their lives being dependent on others if options are available. Independent living and quality of life are vital components for the psychological, as well as economic, well-being of patients with diabetes mellitus.

A need therefore exists for an improved medication delivery method and apparatus.

SUMMARY OF THE INVENTION

In accordance with at least one presently preferred embodiment of the present invention, there is broadly contemplated a system that enables insulin-dependent diabetics to safely administer their daily dosages of medication using pre-filled syringes.

In summary, one aspect of the invention provides a medication delivery system comprising: an arrangement for delivering pre-determined dosages of medication; said arrangement having indicia indicating the dosage to be delivered; an arrangement for organizing said delivery arrangements; and said organizing arrangement having indicia corresponding to the indicia of said delivery arrangements.

Another aspect of the present invention provides an apparatus for delivering medication comprising: a barrel containing a pre-determined dosage of medication; a plunger, slidably mounted within said barrel, and extending from the plunger end of said barrel; a needle for delivering medication extending from the needle end of the barrel; said apparatus having indicia indicating the dosage of medication to be delivered.

An additional aspect of the present invention provides a medication storage and organization system comprising: an arrangement for storing organizing arrangements for delivering pre-determined dosages of medication; said arrangement for storing and organizing having indicia indicating the pre-determined dosages of medication contained in the arrangements for delivering the pre-determined dosages of medication.

Furthermore, an additional aspect of the invention provides a glucometer comprising: an arrangement for accepting a sample of a patient's blood; an arrangement for determining a patient's blood sugar range; an arrangement for displaying said range; and said display comprising indicia.

For a better understanding of the present invention, together with other and further features and advantages thereof, reference is made to the following description, taken in conjunction with the accompanying drawings, and the scope of the invention that will be pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates a plurality of color-distinctive syringe plungers with stoppers attached.

FIG. 2 illustrates a plurality of color-distinctive syringe caps.

FIG. 3B illustrates a completed color-coded medication chart.

FIG. 4A illustrates a plurality of color-distinctive syringes without caps attached.

DETAILED DESCRIPTION OF THE PREFERRED EMBODIMENTS

The presently preferred embodiment of the present invention will now be described. In the preferred embodiment, there is described color-distinctive components that, when combined with an apparatus and system of use, enable insulin dependent diabetics a safe and easy way to control their blood glucose levels. It will be appreciated that the present invention is useful for diabetics who would benefit from the use of a sliding scale of insulin to control their diabetes. Though the invention may be described in connection with insulin, it may be used for any timed medication regimen.

Figure 3A:
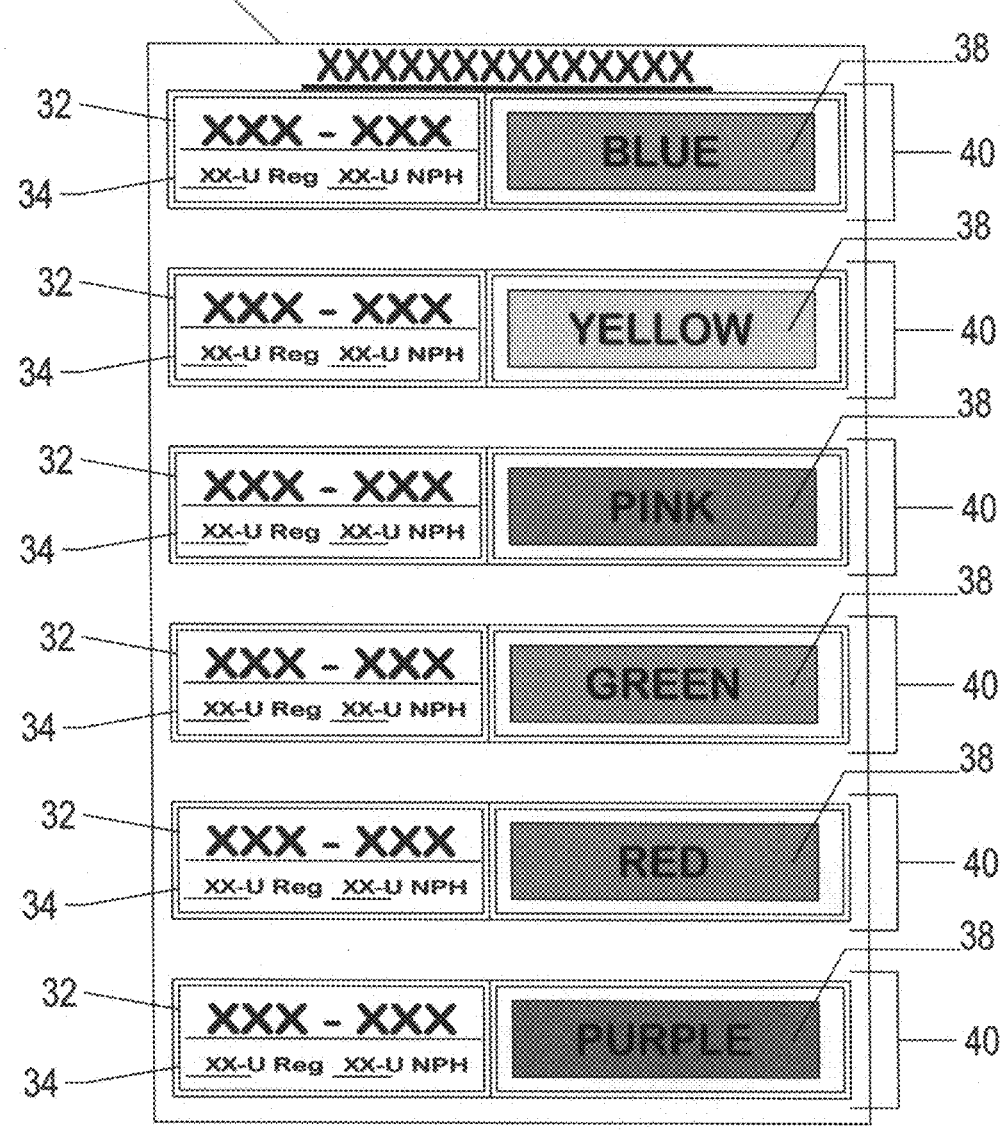
FIG. 3A illustrates an example of a color-coded medication chart

Turning now to the drawings, FIG. 1 illustrates a plurality of syringe plunger rods with attached stoppers 22. FIG. 2 illustrates a plurality of syringe caps 24. FIGS. 3A and 3B illustrate a color-coded medication chart 20 whereby blood glucose parameters 32, match color-distinctive syringe components 22 and 24, corresponding to correct insulin doses 34. Each color is representative of a specific set of blood glucose parameters and corresponding insulin doses as prescribed by a physician.

Figure 4B:
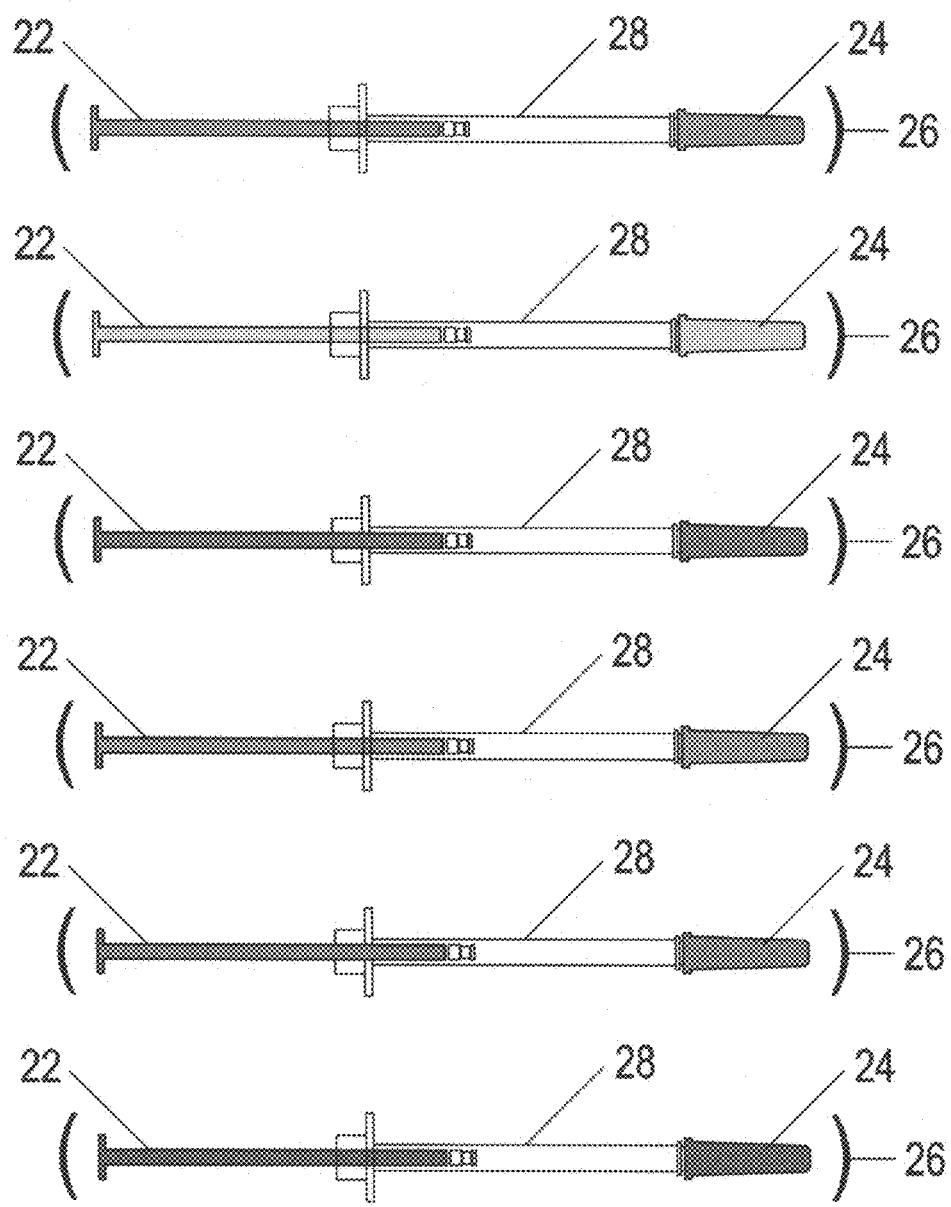
FIG. 4B illustrates a plurality of color-distinctive syringes with caps attached.
Figure 4C:
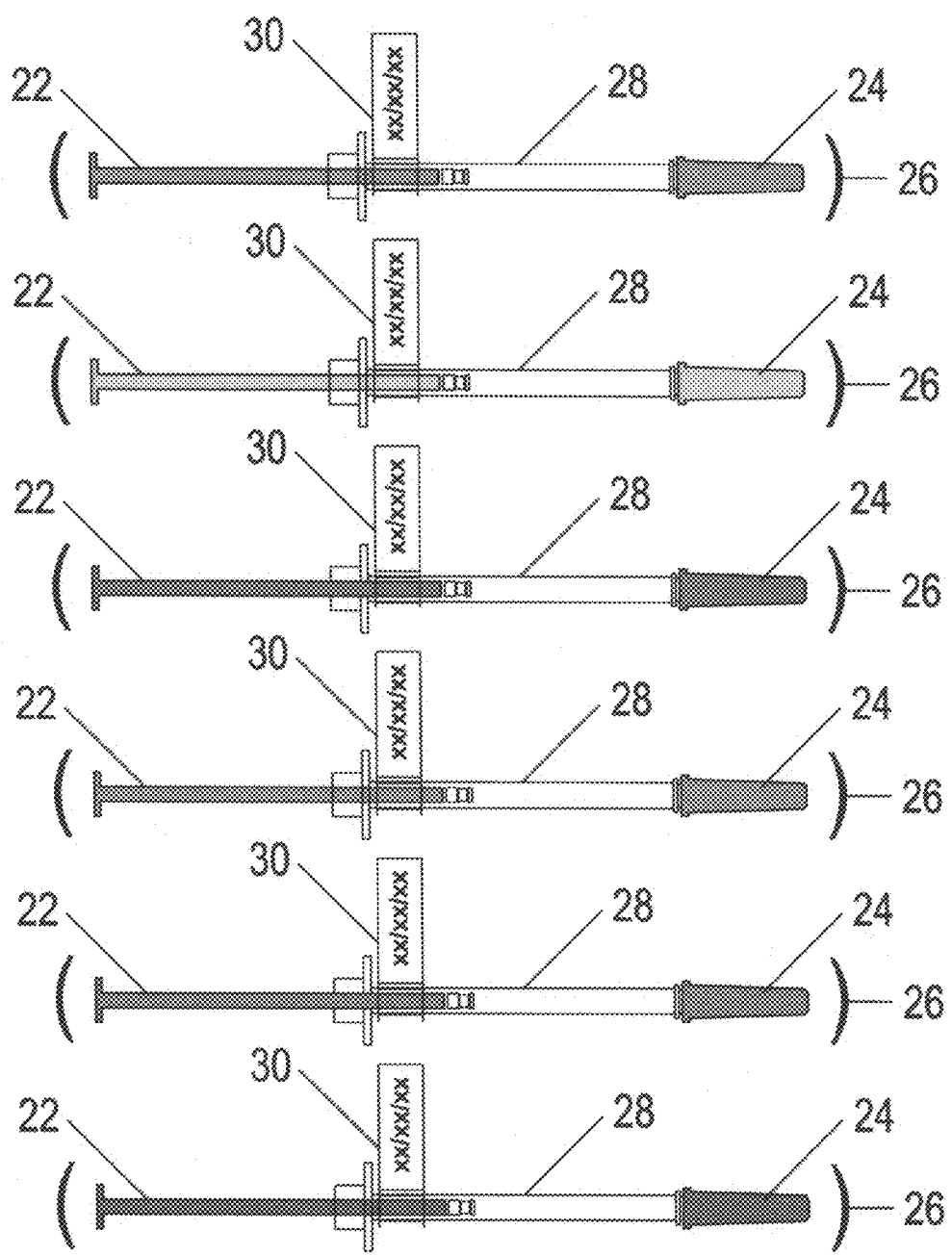
FIG. 4C illustrates a plurality of color-distinctive syringes with labels attached.

FIGS. 4A-4C illustrate the color-distinctive syringe components. Preferably, the colors used will be from the group principally composed of blue, yellow, pink, green, red, and purple. Colors specified in the drawings are representative of possible color choices. It will be appreciated that colors are not limited to those depicted here and could be customized for optical acuity in patients with visual impairment. Though other colors may be substituted, the preferred colors are known to be more easily visualized by individuals with impaired sight.

Each color-distinctive syringe plunger rod with attached stopper 22 functions as the method for withdrawing insulin into the syringe in preparation for injection. The color-distinctive plunger rod with attached stopper provides greater visual contrast within the syringe barrel 28 thus providing an enhanced mechanism for visually impaired persons with diabetes to prepare their medication. The matching color cap 24 is embodied as an added safety measure for selecting medication dose as well as a safety mechanism for covering the needle portion of each syringe. Production of the color-distinctive syringe components will utilize existing pharmaceutical grade resilient materials and manufacturing processes also not included in this specification but known to those skilled in the art.

In another embodiment of the present invention, an expiration label 30 (FIG. 4C) may be attached to the barrel of said syringe to record the expiration date of insulin contained within the pre-filled syringe if applicable.

FIGS. 3A and 3B illustrate another embodiment of the invention, the color-coded chart 20. Each section of the medication chart 40 is designed as a replaceable adhesive label to allow for changes in the patient's prescribed insulin regimen. The label is preferably divided into two sections: the left portion incorporates designated areas for transcription of physician's blood glucose parameters 32 and corresponding insulin dose 34. The right side of each label may be comprised of a color-coded block 38. Each color block represents a different set of blood glucose parameters and corresponding prescribed insulin doses. As an added safety measure, a printed description of each color may be transposed over each color-coded block. To accommodate changes in prescribed doses and parameters, extra sheets of replacement labels FIG.

6 may be provided with the system. The charts are designed with an adhesive backing for correct placement within the system as described in further embodiments.

Figure 5:
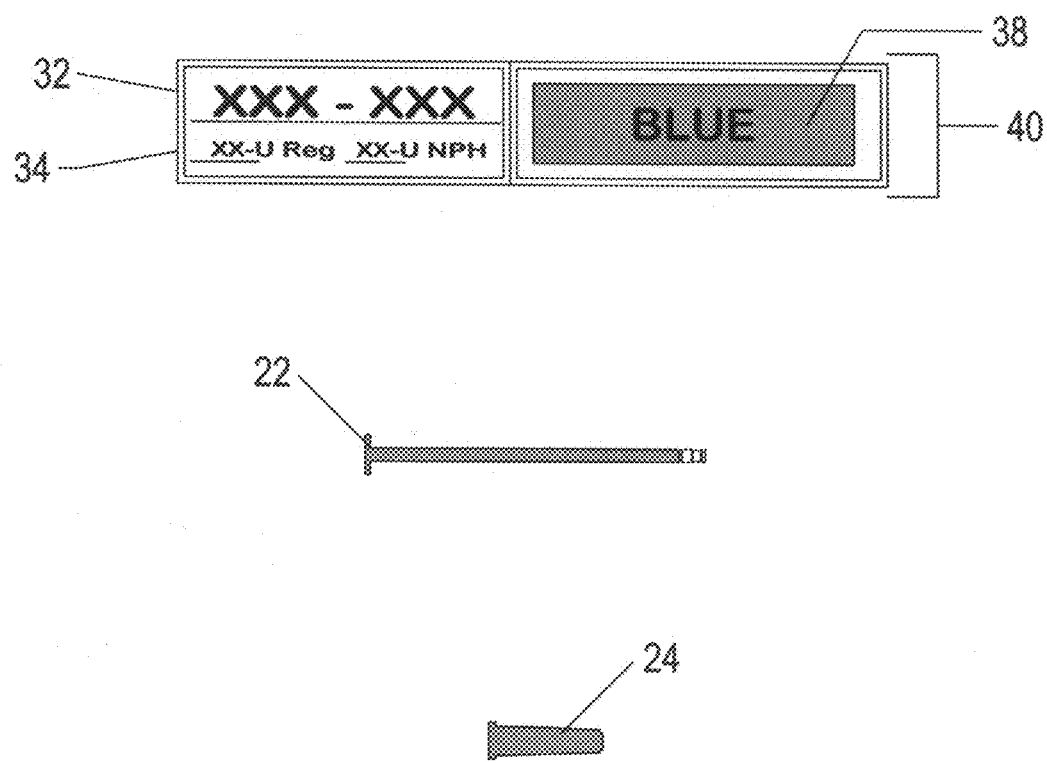
FIG. 5 illustrates a set of matching color-distinctive and color-coded system components.

An example of color-coordinated components is shown in FIG. 5. A color-distinctive plunger rod with attached stopper 22, color-distinctive cap 24, and color-coded medication chart label 40, all corresponding to a specific insulin dose 34 and blood glucose level 32, are shown.

Figure 7A:
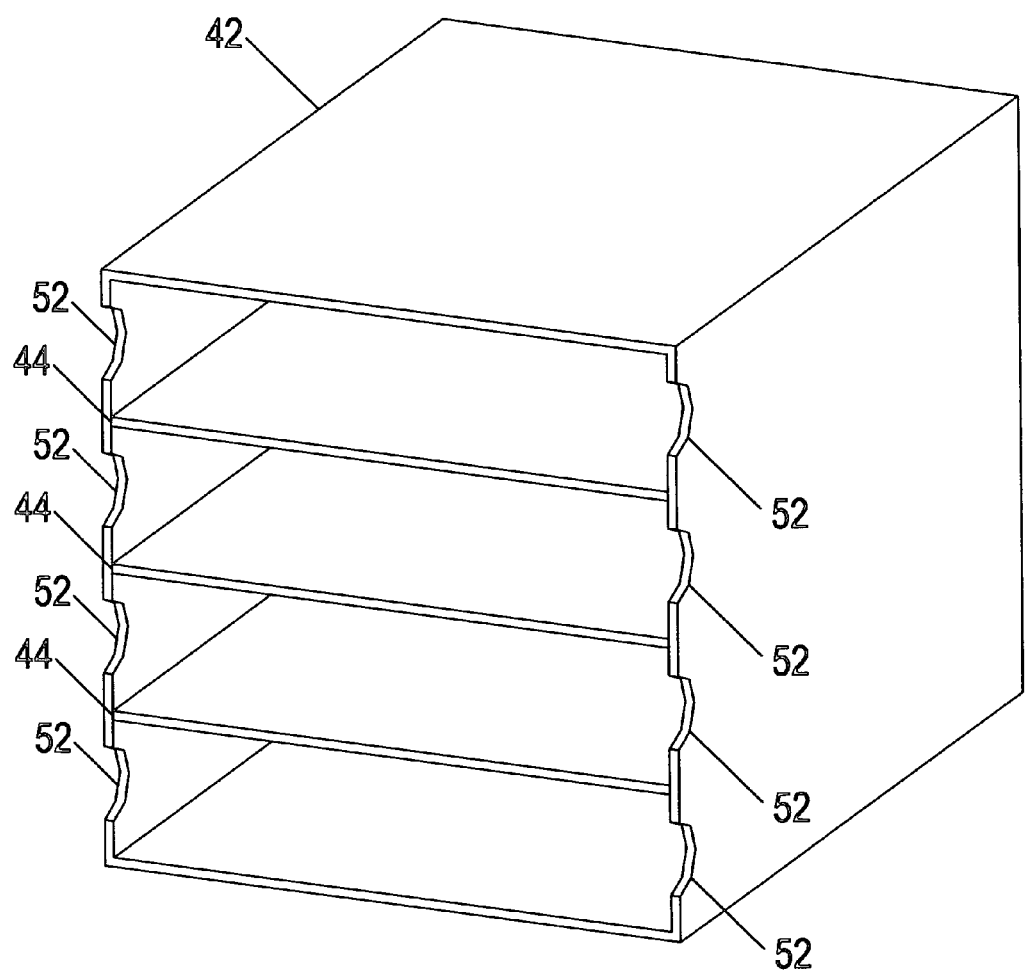
FIG. 7A illustrates a front view of the main storage compartment as it would look without drawers.
Figure 7B:
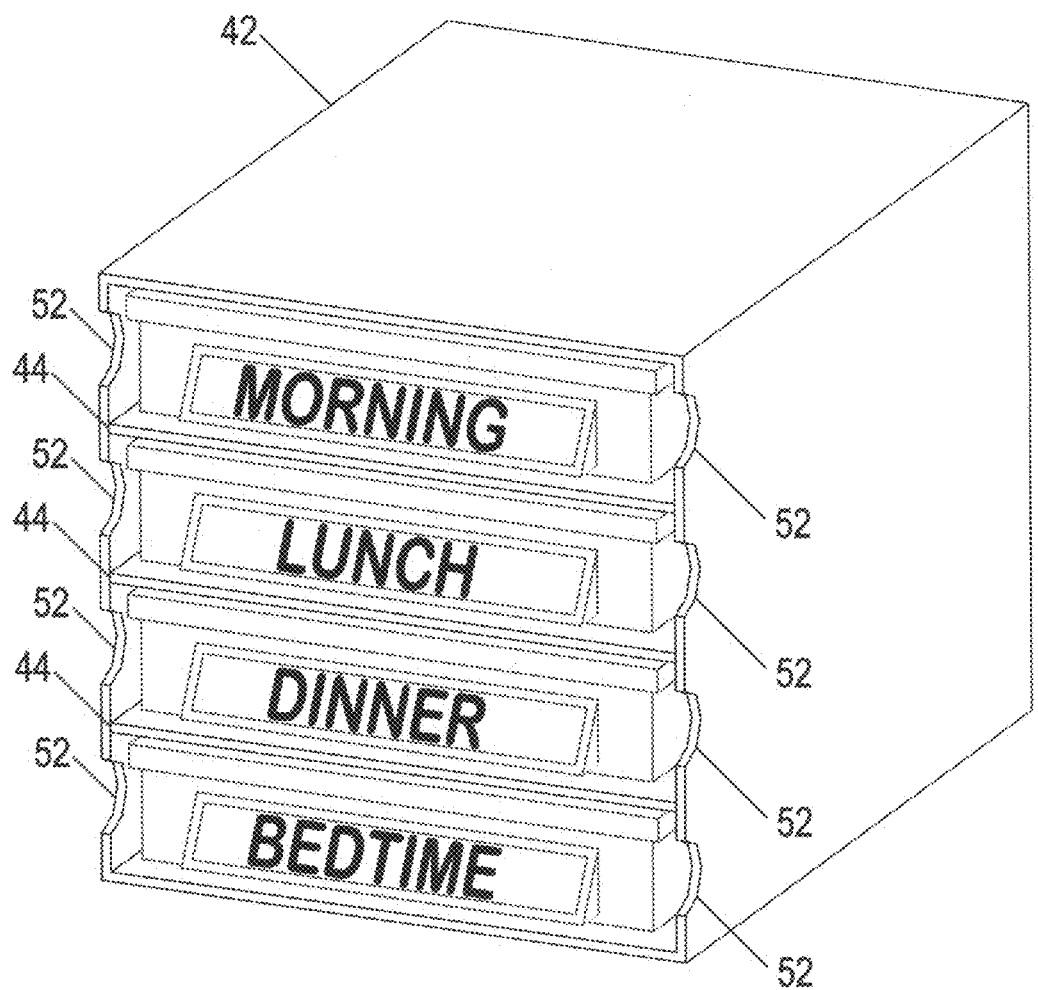
FIG. 7B illustrates a front, top and side view of the main storage unit as it appears when system is complete.

In another embodiment of the invention, a main storage unit FIGS. 7A and 7B serves as a method of containment for the complete system. The outer shell 42 consists of a substantially rigid material and defines an interior having an opening to provide access for one or a plurality of shelving supports 44. Preferably, notches 52 may be incorporated into the sides of the main storage unit allowing removal and replacement of individual medication drawers described below. Generally, insulin must be stored at temperatures between 2 degrees and 8 degrees centigrade. For this reason the main storage unit is preferably of a size and shape allowing placement in most refrigerators.

Figure 8A:
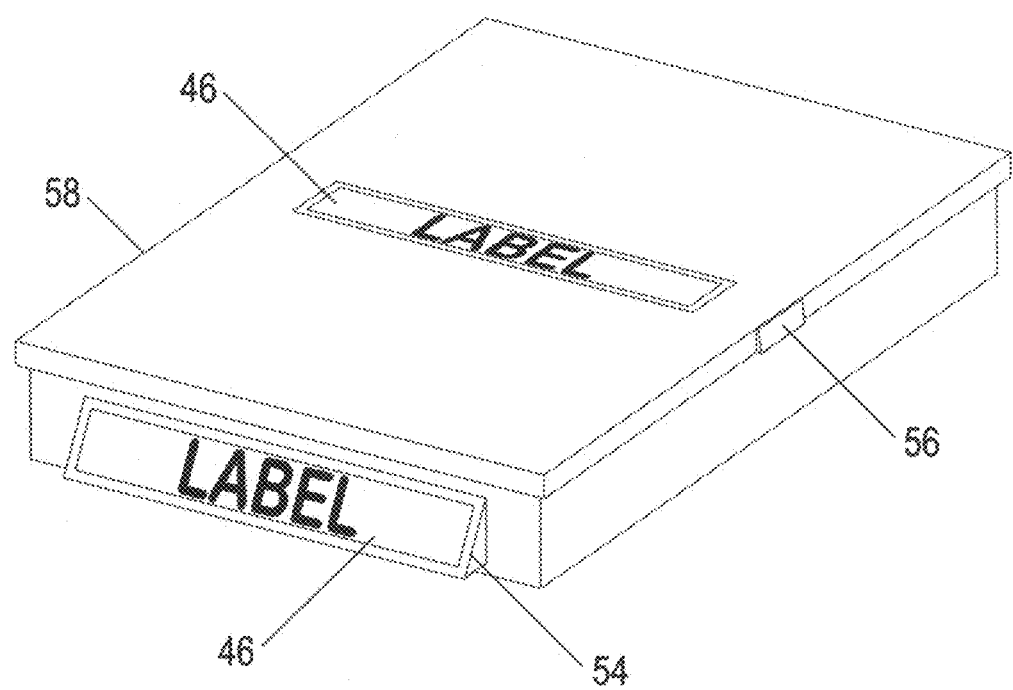
FIG. 8A illustrates a top and front view of a closed medication drawer before large chronological labels are attached.

Another embodiment of the invention incorporates a medication drawer depicted in FIGS. 8A to 8E, or a plurality of medication drawers, as the method of storage and organization for the color-distinctive syringe and chart system. As illustrated in FIG. 8A, each drawer is preferably constructed of a substantially rigid material and consists of a lid 58 and a storage containment area separated into compartments 60 (FIG. 8B) whereby the color-distinctive syringes are stored in dose order. Each compartment is preferably designed to contain a plurality of pre-filled, color-distinctive syringes.

In another embodiment of the invention, each drawer may incorporate an angled handle 54 into the front aspect of said drawer enabling easy accessibility for physically challenged users. For added safety, each drawer may be boldly labeled according to dose time. Two adhesive pre-printed large labels 48 (FIGS. 7B and 8C) for each dose time may be included with the system. As shown in FIG. 8A (before labels are attached), preferably, there are two areas on each drawer designated for label placement. Preferably, the word "LABEL" 46 is imprinted in the plastic surface in two places as a guide for placement of the labels. One is adhered to the top of the closed lid 58 of each drawer and the other label is adhered to the front handle 54 of each drawer. It will be understood that the number of drawers in each main storage unit is determined by the number of times per day the diabetic administers his/her medication as prescribed by a physician. Main storage unit size is determined by number of drawers required and may be adapted with changes in medication regimen. The drawer or drawers are arranged within the main storage unit FIG. 7B in chronological order.

Figure 8B:
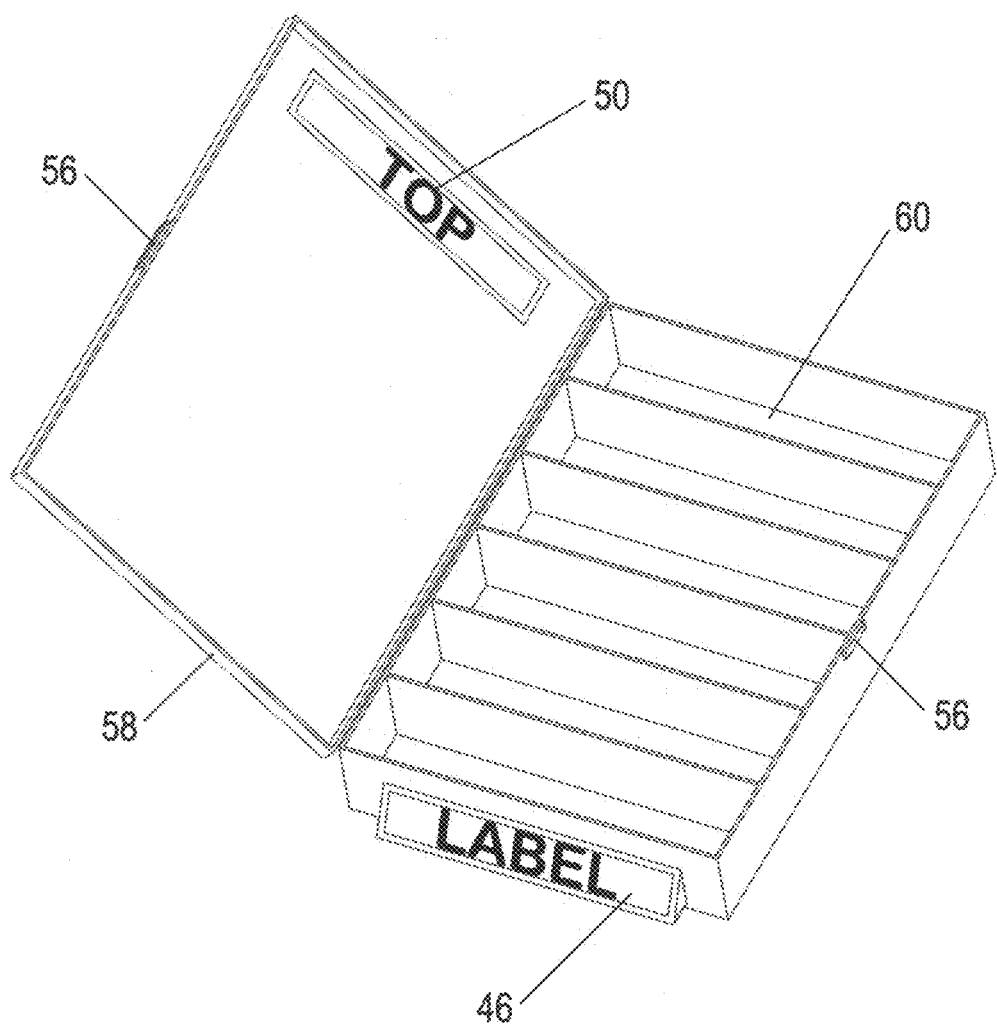
FIG. 8B illustrates an open view of a medication drawer as it appears prior to assembly.
Figure 8C:
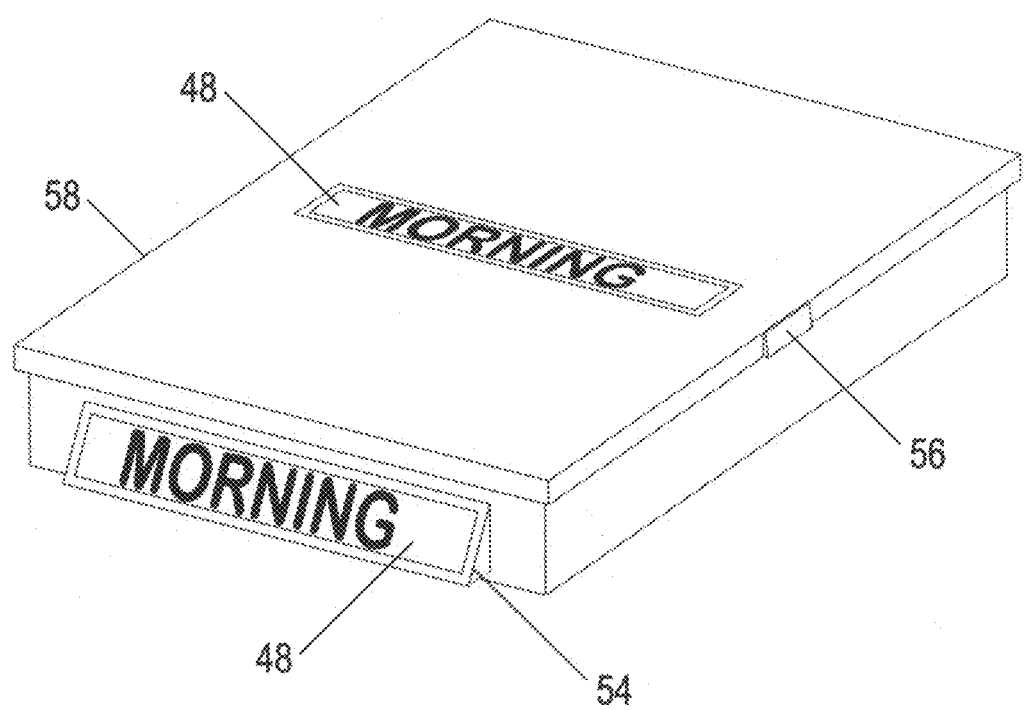
FIG. 8C illustrates a closed top and front view of a medication drawer after large chronological labels are attached.
Figure 8D:
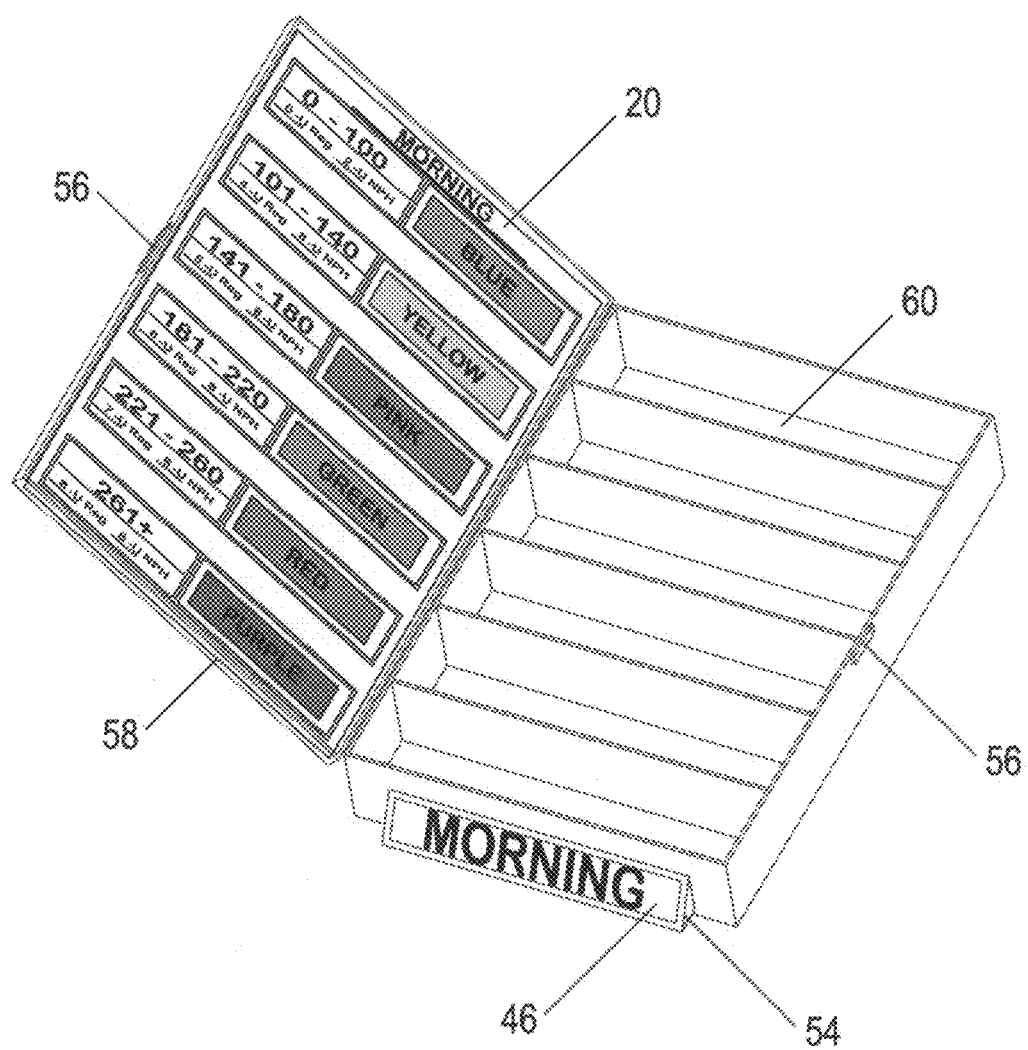
FIG. 8D illustrates an open view of a medication drawer with a completed color-coded chart attached to inner lid.

FIG. 8A illustrates a closed drawer before labeling occurs. FIG. 8B illustrates an open drawer. A lid securing mechanism 56 (FIGS. 8A-8D), made of a substantially rigid material, may be used for securing the medication drawer contents and to make access difficult for children.

Figure 8E:
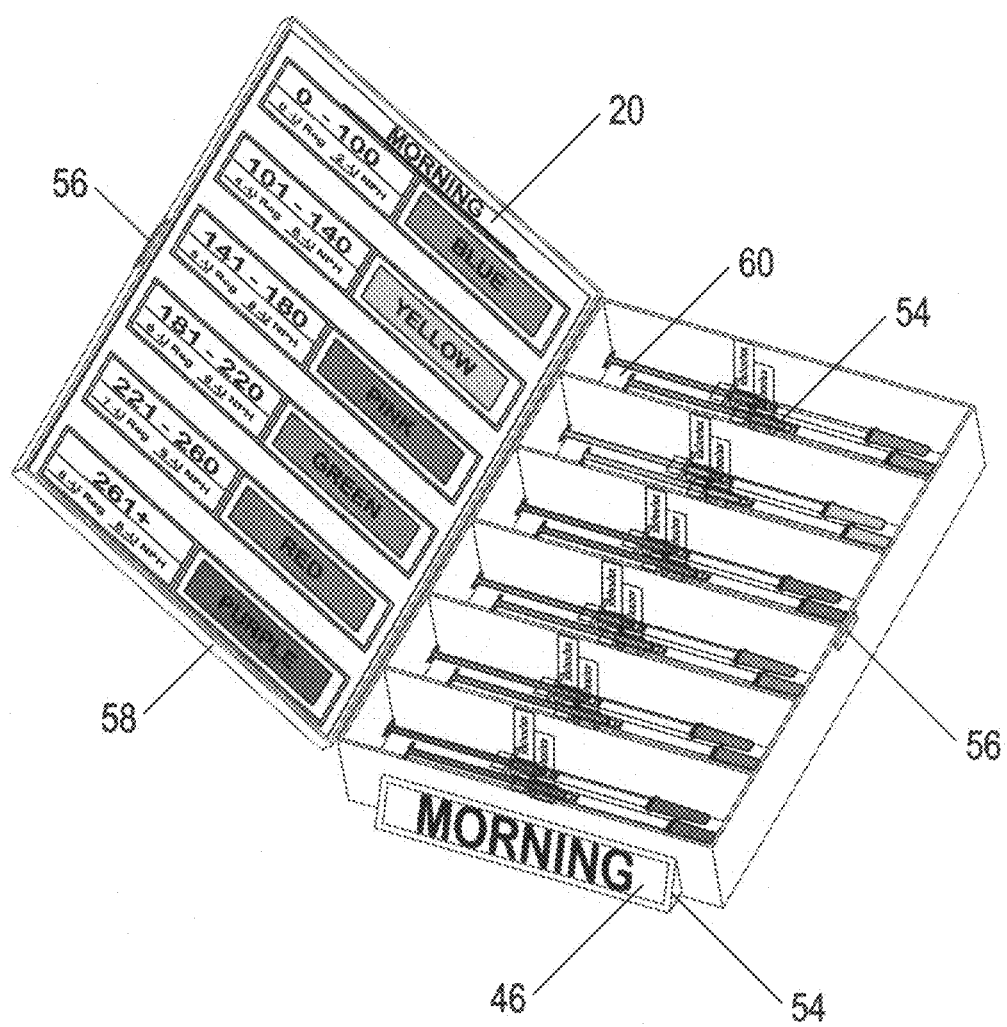
FIG. 8E illustrates an open view of a medication drawer as it appears when system is complete.

FIG. 8E is an illustration of an open view of a medication drawer as it would appear when the system is ready for use by patient. It illustrates the inner surface of the lid, with color-coded chart attached 20, aligned with compartments 60 containing corresponding color-distinctive syringes.

In accordance with the present invention, the system is set up by first removing each drawer FIG. 8A from main storage unit FIG. 7B and adhering two pre-printed large labels 48 indicating medication dose times over the areas marked "LABEL" 46 (FIGS. 8A and 8B). The main storage unit FIGS. 7A and 7B is designed to accommodate from one to a plurality of medication drawers, dependent upon the number of times a person with diabetes requires insulin throughout the day.

Figure 6:
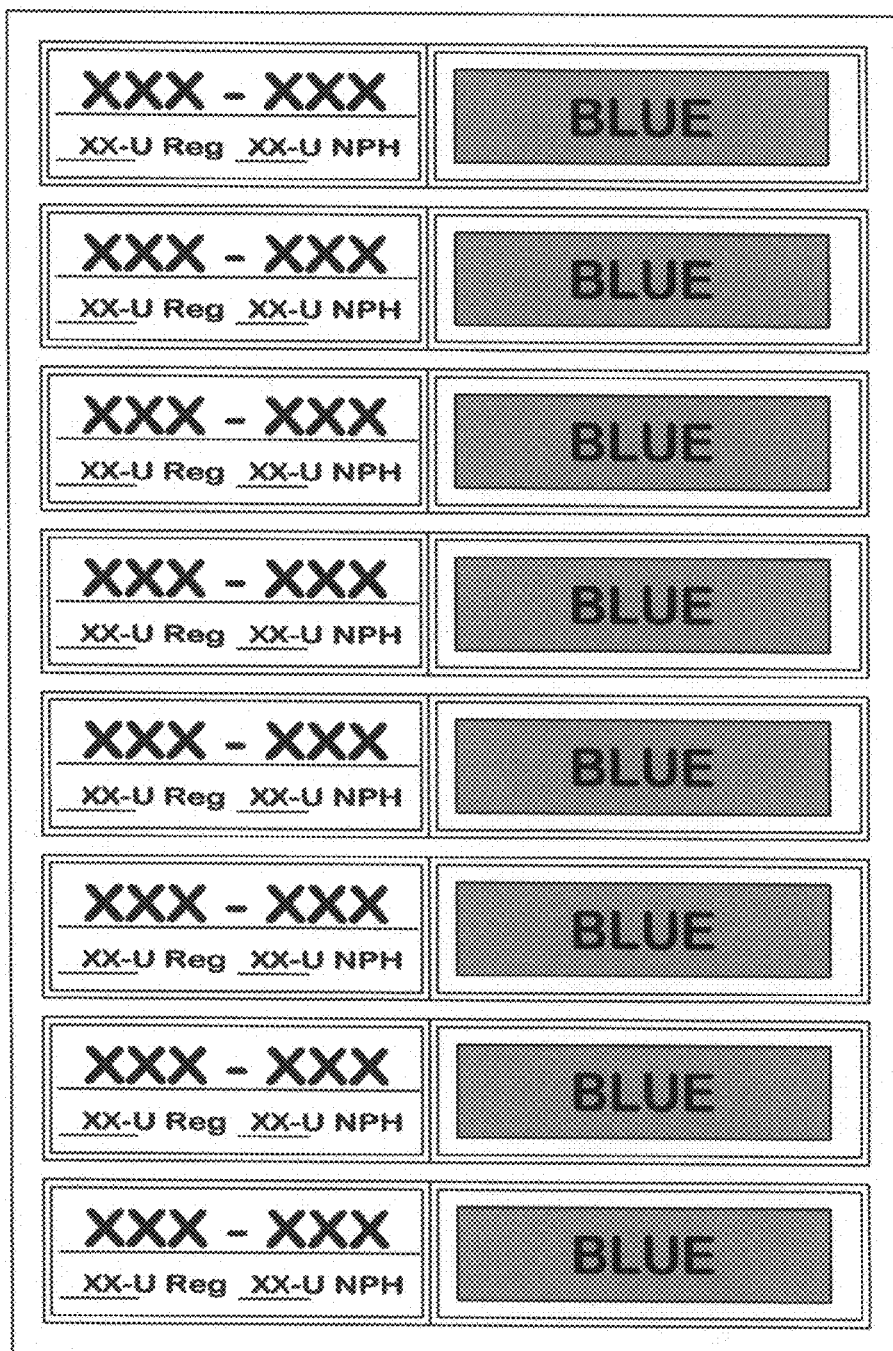
FIG. 6 illustrates a sheet of replaceable color-coded medication labels.

As illustrated in FIG. 3B, prescribed blood glucose parameters 32 and corresponding insulin doses 34 may be transcribed onto each color-coded label 40 of the medication chart. Insulin dose and parameters are typically different for each time of day; therefore, a chart is preferably completed for each drawer in the system. Additional sheets of color-coded labels FIG. 6 may be provided to accommodate insulin dose and glucose parameter changes. The color-coded medication chart 20 (FIG. 8D) is preferably adhered to the inside surface of the lid of its corresponding medication drawer, taking care to align the top of chart with the word "TOP" 50 imprinted on inside surface of the lid of each drawer embodied as a placement guide.

Each color-distinctive syringe FIG. 4B, distinguished by the color of plunger rod with attached stopper 22, and matching color cap 24, is filled with the correct dose of insulin 34 (FIG. 3B) as recorded on the same color label 40 of medication chart.

Due to manufacturer specifications some insulin may have an expiration date. If such a date is applicable, it is preferably recorded on the expiration label 30 (FIG. 4C) and then attached to each syringe. The number of syringes of each color to be filled may be dependent upon the diabetic's history of use, number of days the diabetic may be without assistance, and insulin manufacturer's recommended storage guidelines.

The pre-filled, color-distinctive syringes may be placed in the medication drawer in compartments 60 that align with the same colors of the medication chart 20 (FIG. 8E), thus coordinating the diabetic's blood glucose level 32 with the syringe containing his/her prescribed dose of insulin. After all syringes have been filled and placed in the appropriate compartments, the lid of each drawer may be closed and securely latched 56 to prevent spillage of contents and inadvertent tampering by children. The drawer may be then returned to its proper placement within the main storage unit FIG. 7B. The process may be repeated until all medication drawers are completed. The entire main storage unit is then preferably placed in refrigeration per insulin manufacturer's guidelines.

At medication time, the person with diabetes removes the appropriate drawer FIG. 7B from the main storage unit. The diabetic then determines his/her blood glucose level using a glucometer of choice. The glucometer displays the diabetic's blood glucose result. The diabetic then selects the label color, from the selection of color-coded labels on medication chart 20, that matches the range for this blood glucose reading. He/she then chooses the color-distinctive syringe 26 that corresponds to the chart color of his/her blood glucose level 32, thus administering the correct dose of insulin 34.

Another obstacle for diabetic patients is seen in obtaining proper blood glucose levels. To properly select the correct dosage of insulin, a glucometer is utilized. A glucometer is an apparatus for determining blood glucose levels and is recognized as a standard of blood glucose evaluation by those skilled in the art. A sample of the patient's blood is drawn, placed into the glucometer, and the glucometer indicates the patient's blood glucose level. Traditionally, the glucometer indicates this reading in some type of number format. Often, persons with impaired senses or mental function are either unable to read the glucometer properly or cannot chose the correct dosage of medication based upon the glucometer results. In one embodiment of the present invention, the glucometer displays an appropriate color for the patient's blood glucose reading. The color would correspond to the appropriate color-coded syringe.

The disclosure now turns to an exemplary discussion of the usage of the present invention.

Using a glucometer, the diabetic determines that his/her morning blood glucose level is 120. The diabetic removes the MORNING drawer from the main storage unit FIG. 7B and opens the drawer FIG. 8E displaying the color-coded blood glucose chart 20 and corresponding pre-filled syringes 26. As prescribed in this illustration, glucose levels ranging between 101-140 (32) are indicated by both the color block, 38 and the word, YELLOW, incorporated on a label of the color-coded medication chart 20. The patient then matches the YELLOW color on chart to the YELLOW color-distinctive syringe 26, thus administering his/her correct dose of insulin. Though the preferred embodiment uses the indicia of color to coordinate, organize and properly select the pre-determined dosages of medication, it will be appreciated that any type of indicia may be used. Examples of useful indicia include, but are not limited to, numbers, letters, graphic symbols, Braille, and machine readable bar codes. It is will also be appreciated that, although administration of medications for diabetics is discussed in detail throughout this application, the apparatus and method is applicable to the use of any type of medications that must be administered multiple times in varying doses throughout the day.

If not otherwise stated herein, it is to be assumed that all patents, patent applications, patent publications and other publications (including web-based publications) mentioned and cited herein are hereby fully incorporated by reference herein as if set forth in their entirety.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A medication delivery system comprising:
   a plurality of indicia-coded and pre-filled syringes for delivering a predetermined dose or dosages of medication; said plurality of indicia-coded syringes having a predetermined dose or dosages of medication therein and indicia of said predetermined dose or dosages of medication thereon;
   an apparatus for quantitative measurement of blood glucose or other biological body substances wherein said measurement is displayed as indicia corresponding to said indicia of said plurality of indicia-coded and pre-filled syringes; and
   storage unit comprising trays with compartments for organizing and storing said plurality of indicia-coded and pre-filled syringes, said compartments having indicia corresponding to said indicia of said indicia-coded and pre-filled syringes and further corresponding to said indicia of said apparatus display.

2. The medication delivery system of claim 1, wherein said corresponding indicia of said plurality of indicia-coded and pre-filled syringes said storage unit tray compartments and said apparatus display are color based.

3. The medication delivery system of claim 1, wherein said corresponding indicia of said plurality of indicia-coded and pre-filled syringes, said storage unit tray compartments and said apparatus display are tactile based.

4. The medication system of claim 1, wherein said corresponding indicia of said plurality of indicia-coded and pre-filled syringes, said storage unit tray compartments and said apparatus display are selected from a group consisting of colors, numbers, letters, graphic symbols, tactile symbols, machine readable bar codes or any combination thereof 5. The medication delivery system of claim 1, wherein said plurality of indicia-coded and pre-filled syringes for delivering a predetermined dose or dosages of medication, wherein said medication is insulin.

* * * * *